United States Patent [19]

Olney

[11] Patent Number: 5,039,528
[45] Date of Patent: Aug. 13, 1991

[54] EAA ANTAGONISTS AS ANTI-EMETIC DRUGS

[76] Inventor: John W. Olney, 1 Lorenzo La., St. Louis, Mo. 63124

[21] Appl. No.: 448,767

[22] Filed: Dec. 11, 1989

[51] Int. Cl.$^5$ ................. A61K 9/48; A61K 49/00; A61F 13/00
[52] U.S. Cl. ................. 424/451; 424/422; 424/10; 514/872; 514/922
[58] Field of Search ................. 424/10, 451, 422; 514/249, 872, 922

[56] References Cited

U.S. PATENT DOCUMENTS

| | | | |
|---|---|---|---|
| 3,976,774 | 8/1976 | Conway | 424/250 |
| 4,126,687 | 11/1978 | Vandenberk et al. | 424/267 |
| 4,213,983 | 7/1980 | Hadley et al. | 424/250 |
| 4,302,452 | 11/1981 | Pittman | 424/243 |
| 4,351,833 | 9/1982 | Johnson | 424/248.5 |
| 4,466,968 | 8/1984 | Bernstein | 424/260 |
| 4,717,563 | 1/1988 | Alphin et al. | 424/10 |
| 4,753,789 | 6/1988 | Tyers et al. | 424/10 |
| 4,861,781 | 8/1989 | Goldberg | 514/282 |

OTHER PUBLICATIONS

Florczyck, A. P., et al, "Cisplatin induced emesis in the ferret: a new animal model," *Cancer Treatment Reports* 66: 187–190 (1982).
Davies, J., et al, "Recent Advances in the Pharmacology of Excitatory Amino Acids in the Mammalian Central Nervous System," in *Excitotoxins*, edited by K. Fuxe et al (Macmillan Press, London, 1983).
Boast, C. A., "Neuroprotection after brain ischemia: role of competitive NMDA antagonists," *Neurology and Neurobiology* 46: 691–698 (1988).
Herrling, P. L., et al., "NMDA antagonistic properties of the enantiomers of CPP and CPP-ene," *Soc. Neurosci. Abstr.* 15: 327 (1989).
Honore, T., et al, "Quinoxalinediones: potent competitive non-NMDA glutamate receptor antagonists," *Science* 241: 701–703 (1988).
Drejer, J. and Honore, T., "New quinoxalinediones show potent antagonism of quisqualate responses in cultured mouse cortical neurons," *Neurosci. Letters* 87: 104–108 (1988).
Honore, T., et al, "Quisqualate receptor specific quinoxalinedione (FG 9202, NBQX) blocks kainate induced responses," *J. Neurochem.* 52: Suppl., S42-A (1989).
Sheardown, M. J., et al, "NBQX, a specific non-NMDA receptor antagonist, shows neuroprotective effects against cerebral ischemia," abstract published in Proceedings of the First International Conference on Therapy with Amino Acids and Analogs, Vienna, Aug. 7–12, 1989.

*Primary Examiner*—Thurman K. Page
*Assistant Examiner*—G. Kishore
*Attorney, Agent, or Firm*—Haverstock, Garrett and Roberts

[57] ABSTRACT

This invention relates to a method and a class of pharmaceutical agents for suppressing vomiting, nausea, and other emetic symptoms. The method involves administering to a susceptible mammal a glutamate (EAA) receptor antagonist at an anti-emetically effective dose which does not cause undesirable side effects. Preferred EAA antagonists include those that do not readily cross blood-brain barriers (BBB). One suitable formulation comprises a broad-spectrum antagonist such as kynurenic acid or 7-chlorokynurenate. Other formulations include EAA antagonists that preferentially block NMDA receptors (such as D-AP5) or non-NMDA receptors (such as CNQX), or mixtures thereof that can block both classes of EAA receptors. In lab tests, the agents of this invention were shown to reduce or entirely block the effects of several emetic agents, including cisplatin. Treated animals did not vomit or exhibit lethargy or malaise and did not display any adverse side effects, while control animals consistently displayed lethargy, malaise, and vomiting.

18 Claims, No Drawings

EAA ANTAGONISTS AS ANTI-EMETIC DRUGS

FIELD OF THE INVENTION

This invention is in the field of pharmacology, and relates to anti-emetic drugs, i.e., drugs that suppress nausea and vomiting.

BACKGROUND OF THE INVENTION

"Emesis" and "emetic" refer to the process commonly known as vomiting or retching, wherein the stomach is evacuated through the esophagus and mouth due to strong muscular contractions in the abdomen. Emesis is usually accompanied by nausea and feelings of strong malaise and discomfort. As used herein, emesis includes vomiting and its related symptoms, such as nausea and malaise.

Emesis can be caused or aggravated by a range of factors, including food poisoning, irritation of the gastrointestinal tract or the nerves that innervate this tract, motion sickness, or severe anxiety. It can also be an undesired side effect of some pharmacological and medical treatments, especially cancer chemotherapy, and radiation therapy. When caused by food poisoning, emesis can be helpful and useful, since it evacuates the stomach and can remove toxins or detrimental microbes. However, in most other situations, emesis is intensely unpleasant and unhelpful. It can be a major problem and can even become life-threatening for people who are already suffering from cancer or other life-threatening illnesses, since it can prevent them from obtaining proper nutrition.

The mechanisms by which vomiting is induced are complex and are not fully understood. However, most cases are believed to involve a reflex circuit, commonly called a reflex "arc," consisting of nerve cells which are linked in series such that when a nerve cell on the receptive end of the arc receives a message, it relays the message on to other nerve cells leading into an emesis center in the brain stem. In the emesis center, nerve cells which are part of the reflex circuit interpret the message and act upon it. For example, the message may have come from sensory cells in the inner ear and may pertain to excessive abnormal motion which, for reasons that are poorly understood, is interpreted by the emesis center as a basis for sending an outgoing command through nerve fibers to muscles in the gastrointestinal tract and abdominal wall. This initiates a coordinated pattern of muscle contractions that constitute the act of vomiting, representing the condition known as motion sickness.

Alternatively, a message may originate in sensory receptors in the gut wall pertaining to a stimulus that is irritating to the gastrointestinal tract. This message is conveyed through nerve fibers from the gut to the emesis center in the brain stem and interpreted as basis for initiating the same outgoing command to commence the act of vomiting. The emesis center functions like a "central switchboard" that serves as the central hub for the incoming and outgoing segments of numerous reflex arcs pertaining to both normal and abnormal gastrointestinal motility, normal motility being the peristaltic wave movements of the gut wall that facilitate processing of food, and abnormal motility being reverse peristaltic movements that are first perceived as nausea and then, as they become more vigorous, as retching and/or vomiting.

Under conditions of extreme anxiety or stress, messages from higher brain centers pertaining to a feeling of being overwhelmed or defeated are conveyed to the emesis center which may interpret the situation as a basis for emesis, perhaps as a primitive response intended to purge the organism of whatever is causing the stress.

An emesis chemoreceptor trigger (ECT) zone has been identified (Borison and Brizzee, 1951; Borison and Wang, 1953) in the same general region of the brain stem where the emesis center is located. The ECT zone is located specifically in a region designated anatomically as the area postrema, which is recognized as one of several circumventricular organs (CVO's) that exist within the brain. CVO's are specialized brain regions that are distinguished from all other regions of the central nervous system (CNS) by the fact that they do not have blood brain barriers (BBB) to prevent substances circulating in the blood from freely entering these brain regions (Rapoport, 1976). Thus, unlike the remainder of the CNS which has BBB that screen substances and only allow certain agents to enter, CVO's are freely accessible to any substances circulating in the blood.

It has been postulated that neurons in the area postrema ECT zone serve as sensors of noxious substances circulating in the blood. Thus, after such a substance has been ingested and begins to be absorbed into the blood, it will enter the area postrema ECT zone and be sensed as a harmful substance. That triggers a message to evacuate the gastrointestinal tract, thereby ridding the body of any remaining noxious substance in the gut. Whether the ECT zone truly functions in this manner is not well established. However, it appears clear that ECT neurons, like other neurons in the general region of the brain stem emesis center, can mediate the act of vomiting.

In the study of potential anti-emetic drugs, the lab animals appropriate for use are ferrets, dogs, cats and monkeys, since these species have a vomit reflex comparable to humans. Rodents and rabbits are not used, since they do not have such a vomit mechanism. Ferrets have become the preferred specie for such research; although they are smaller, less expensive, and require smaller amounts of drugs (some of which are scarce and quite expensive) than dogs or monkeys, ferrets respond in a similar manner (by exhibiting active vomiting as well as malaise and lethargy) to emetic stimuli that induce symptoms in dogs, monkeys, and humans (Florczyk et al, 1982).

As used herein, terms such as "anti-emetic" and "suppression of emesis" apply to a pharmaceutical agent that can reduce, ameliorate, or eliminate one or more symptoms of at least one type of emesis. Various efforts have been made to develop anti-emetic drugs. However, most drugs developed to date are only weakly or moderately effective as anti-emetics and are useful for controlling only certain types of emesis. Moreover, since most such agents interact with many physiological systems in addition to those relevant to the regulation of vomiting, they tend to have undesirable side effects when used at doses required to suppress nausea and vomiting.

Drugs classified as anti-histaminics, such as dimenhydrinate (trade name Dramamine), and anticholinergics, such as scopalamine, have been used for years to prevent motion sickness or the related condition, vertigo (dizziness), which is a prominent symptom of Meniere's disease. However, these agents are relatively ineffective unless taken before a boat or airplane ride or other motion begins, or before the onset of vertigo in Meniere's disease. In addition, they are not effective in suppressing nausea and vomiting caused by other factors (Goodman and Gilman, 1975).

Several approaches have been employed for ameliorating nausea and vomiting associated with cancer chemotherapy. Traditionally, phenothiazines such as compazine and butyrophenones such as haloperidol have been used because it has been thought that dopamine receptors in brain stem regions associated with the emesis center are involved in vomiting, and these agents block dopamine receptors. Results with these agents have been disappointing; they are only weakly active as anti-emetics and must be used at high doses which stimulate numerous dopamine receptors throughout the brain. This results in severe side effects such as abnormal motor movements, muscle rigidity, and tremors.

Over the past decade, another type of dopamine antagonist, metoclopramide (trade name Reglan) has emerged as the agent of choice for suppressing emesis associated with cancer chemotherapy. Although it represents a moderate improvement over prior therapies, it is only partially effective even when used at doses associated with the same disagreeable side effects that other dopamine receptor antagonists typically cause. Recent evidence suggests that the anti-emetic properties of metoclopramide may be explained, not by an effect at dopamine receptors, but rather by an effect at serotonin receptors. Serotonin is the common name for 5-hydroxytryptamine, 5-HT, and the 5-HT system is often called the serotonergic system. Serotonin receptors are divided into three classes; one class is referred to as 5-HT M receptors. Metoclopramide, in addition to being a dopamine antagonist, is able to antagonize 5-HT M receptors (Miner and Sanger, 1986). Metoclopramide is only a weak 5-HT M receptor antagonist, which explains why it has been an effective anti-emetic only when used at high doses.

Recent evidence suggests that certain other agents within the 5-HT M antagonist class, such as BRL 43694 (which is a more powerful and selective 5-HT M receptor antagonist than metoclopramide), may prove more, useful for controlling nausea and vomiting caused by cancer drug therapy. BRL 43694 was shown to be effective in preventing or reducing the severity of emesis in ferrets treated with cisplatin (Bermudez et al., 1988). Cisplatin is an effective cancer chemotherapy drug; it is also a preferred agent for animal testing of anti-emetic drugs, since it is a particularly strong emetic agent in both humans and certain animals such as the ferret.

Very recently, Cassidy and colleagues (1988) conducted a human clinical trial in which BRL 43694 was administered to 20 cancer patients to test its ability to counteract the emetic properties of various drugs being used to treat cancer. The authors considered the results generally promising in that 7 patients experienced neither nausea nor vomiting, 4 had mild nausea, and 9 patients had both nausea and vomiting but it appeared to be delayed in onset. It is too early to predict whether BRL 43694, or other agents in its class, will represent a substantial improvement over other anti-emetics currently available. A limitation of the study by Cassidy et al is that there was no control group to establish the expected incidence of nausea and vomiting in patients receiving identical cancer chemotherapy without an anti-emetic. Moreover, only 5 of the 20 patients received cisplatin; the others received cancer drugs that are not as strong in emetic properties as cisplatin. Of the 5 patients that received cisplaten, 4 suffered from nausea and vomiting.

While it seems likely that 5-HT M receptor antagonists such as BRL 43694 will prove more effective than anti-emetics previously available for cancer chemotherapy patients, there is still a pressing need for additional agents that are more effective by themselves, or that can be used in conjunction with 5-HT M receptor antagonists to provide better anti-emetic therapy. This goal could best be achieved by finding new agents that prevent nausea and vomiting by a different mechanism than that underlying the anti-emetic properties of the 5-HT M receptor antagonists or other currently available anti-emetics.

It is believed that the locus of action of 5-HT M receptor antagonists is at the level of the gastrointestinal tract (Hawthorn et al., 1988). Enterochromaffin cells in the gut are thought to be irritated (stimulated) by cancer chemotherapy agents, which results in the release of large amounts of 5-HT from these cells. The 5-HT stimulates 5-HT M receptors which are present on nerve endings in the gut wall. This stimulus is communicated through nerve fibers to the emetic center in the brain stem which, as described above, serves as a central switchboard for receiving such messages and responding by initiating a vomit response. By blocking the 5-HT M receptors in the gut, 5-HT M receptor antagonists appear to prevent the message from being relayed from the gut to the emesis center in the brain stem. Therefore, the emesis reflex circuit is broken in its initial segment.

It has also been suggested that the 5-HT M antagonists might act directly upon neurons in the brain stem emesis center (Hawthorn et al 1988). However, there is no evidence to substantiate this proposal, since it has not been possible to demonstrate that there are any 5-HT M receptors in this or any other part of the CNS.

As will be discussed below, in seeking to develop more effective anti-emetics, it would be particularly advantageous if a means could be found for interrupting various types of emesis reflex arcs at the level or location of the central switchboard. Since differing reflex arcs pertaining to different types of emetic stimuli apparently pass through a common point or region in the emesis center in the brain stem, a selective blockade involving that region might be effective in blocking more than one type of emesis reflex. Since this would involve an action by a drug within the CNS, any such action should be regionally selective for the brain stem emesis center and should not involve interactions throughout the remainder of the CNS where unwanted side effects might be generated. A method and a pharmacological agent for achieving this type of anti-emetic therapy is the subject of the invention described herein.

Years ago, it was discovered that two common amino acids, glutamate (the ionized or salt form of glutamic acid, abbreviated Glu) and aspartate (the ionized or salt form of aspartic acid, abbreviated Asp) induce vomiting when present in the blood in high concentrations. The emetic properties of Glu and Asp in humans were first discovered when protein hydrolysates containing high concentrations of these two amino acids were administered intravenously for nutritional purposes to patients who could not take food by mouth. It was found that the hydrolysate solution could not be administered rapidly, or it triggered vomiting. Subsequent studies identified the responsible agents as Glu and Asp (Unna and Howe, 1945; Madden et al., 1945; Levey et al., 1949).

Over the past decade, Glu and Asp, which are present in high concentration in the CNS, have become recognized as major neurotransmitters that account for the vast majority of the excitatory neurotransmitter activity in the mammalian CNS (reviewed by Olney, 1989).

The standard method by which nerve cells communicate with one another and perform the information processing functions of the CNS is by chemical neurotransmission in which a chemical transmitter molecule is released from a fiber ending of a neuron into the extracellular fluid. While in the extracellular fluid, the transmitter molecule acts upon a membrane receptor molecule on the external surface of another neuron. Several chemical transmitter systems have been identified in the mammalian CNS, including the dopaminergic system referred to above, in which dopamine is the transmitter chemical involved, and the serotonergic system, in which 5-HT (a synonym for serotonin) is the transmitter chemical. For each transmitter system, several receptor subtypes have been identified. For example, although 5-HT M receptors have been found only outside the CNS, two other serotonin receptor subtypes have been clearly demonstrated within the CNS, and there are at least two subtypes of dopaminergic receptors in the CNS. The Glu and Asp transmitter systems are exclusively excitatory; i.e., the action of a Glu or Asp molecule at a receptor triggers or facilitates neuronal activity. By contrast, most other transmitter systems, including the dopaminergic and serotonergic systems, are primarily inhibitory (they suppress neuronal activity) and only occasionally excitatory.

Glu and Asp are identical in their excitatory transmitter activities and, since Glu is found in much higher concentration in the CNS than Asp, the Glu/Asp excitatory transmitter system is often referred to as the Glu transmitter system or, alternatively, as the excitatory amino acid (EAA) transmitter system. Certain structural analogs of Glu and Asp, although not found naturally in the CNS, are also referred to as EAA's because they mimic the neuroexcitatory actions of Glu and Asp when brought in contact with EAA neuronal membrane receptors.

Three subtypes of EAA receptors have been identified, each type being named after a certain Glu analog which preferentially binds to and activates that type of receptor. These receptor subtypes are N-methyl-D-aspartate (NMDA) receptors (preferentially sensitive to NMDA), kainic acid (KA) receptors (preferentially sensitive to KA) and quisqualic acid (Quis) receptors (preferentially sensitive to Quis).

In addition to the important neurotransmitter functions performed by Glu and Asp, these compounds are known to have powerful neurotoxic effects (reviewed in Olney, 1989). This was first learned years ago when these compounds were administered subcutaneously to immature animals of various species, including monkeys, and were found to destroy neurons in specific brain regions, referred to above as CVO brain regions. The reason for the neurotoxic reaction being restricted to CVO brain regions is that Glu and Asp are prevented by BBB from entering other brain regions; since CVO regions lack BBB protection, Glu and Asp had free access to neurons in these regions. Subsequent research established that a neuroexcitatory mechanism underlies the neurotoxicity of Glu and Asp. Although Glu and Asp are beneficial and vitally important substances for excitatory neurotransmitter functions in the CNS, if EAA receptors are exposed to these agents in abnormally high concentrations or for prolonged periods, it literally excites the neuron to death. Thus, Glu and Asp are commonly referred to today as excitotoxins.

Although Glu exists in high concentration in the CNS, it is normally confined inside neurons and is released into the extracellular fluid only for transmitting a nerve message from one neuron to another. For this purpose, it is released only in small amounts, and only long enough to contact an EAA synaptic receptor on the surface of another neuron, thereby exciting (i.e., triggering impulse conduction in) the receiving neuron. After impulse conduction, the excitatory action is terminated very quickly by rapid transport of Glu back inside the cell by an energy-dependent transport mechanism. Under abnormal conditions, when energy supply to the brain is deficient (e.g., after a stroke or cardiac arrest, or during perinatal asphyxia), the energy-dependent transport mechanism begins to fail and Glu is allowed to accumulate in abnormal concentrations at EAA receptors. This leads to overstimulation of neurons, which causes them to release more Glu. This can provoke a cascade of Glu release and neuronal hyperstimulation, which can lead to wholesale destruction of CNS neurons.

The involvement of Glu and Asp in these and other possible neurodegenerative disorders has generated a great deal of interest in the development of EAA receptor antagonists as potential neuroprotective drugs which, by blocking EAA receptors, might be able to prevent neuronal degeneration under abnormal conditions such as the above. Numerous agents have been identified that act as specific NMDA receptor antagonists. The majority of these agents, such as D-2-amino-5-phosphonopentanoate (D-AP5), D-2-amino-7-phosphonoheptanoate (D-AP7), CGS 19755, CPP and CPP-ene (Olney, 1989; Boast, 1988; Herrling et al., 1989) do not readily penetrate blood brain barriers and, therefore, have been considered of limited interest as neuroprotective drugs. NMDA antagonists such as phencyclidine (PCP) and MK-801 which readily penetrate BBB have attracted more attention and, in animal experiments, have been shown to exert powerful neuroprotective effects in conditions such as cerebral ischemia (stroke) (Olney, 1989). The ability of these agents to enter brain and interact with NMDA receptors throughout the brain, however, makes them subject to a number of serious side effects, including psychotic disturbances and pathomorphological changes in cerebrocortical neurons (Olney, 1989; Olney et al., 1989).

Fewer advances have been made in developing antagonists for the Quis and KA receptor subtypes. However, kynurenic acid and its chlorinated derivative, 7-chloro-kynurenic acid, are effective broad-spectrum antagonists that block all three subtypes of EAA receptors (NMDA > KA > Quis) (Olney, 1989). Certain types of quinoxalinediones, including 6,7-dinitro-quinoxaline-2,3-dion (DNQX; also referred to as FG 9041) and 6-nitro-7-cyano-quinoxaline-2,3-dion (CNQX; also referred to as FG 9065) were recently described as the first available agents that block non-NMDA receptors substantially more powerfully than NMDA receptors (Honore et al, 1987; also see Honore et al, 1988, and Drejer and Honore, 1988). These quinoxalinediones are significantly more powerful than kynurenic or 7-chloro-kynurenic acid, but neither group has generated much interest as neuroprotective drugs, since they do not penetrate blood-brain barriers.

It is of interest to review the early literature pertaining to Glu and Asp as emetic agents, in light of other information developed more recently regarding their neuroexcitatory and neurotoxic properties. The fact that Glu and Asp, when administered subcutaneously to experimental animals, had neurotoxic effects on neurons confined to CVO brain regions (including the area postrema, which is within the same general brain region where the ECT zone and emetic center are located) signifies that these excitotoxins entered these brain regions and stimulated these neurons, initially causing them to fire nerve impulses excessively, and eventually causing them to die from excessive stimulation. It has been observed in species such as dogs and monkeys, which are subject to an emetic reflex similar to that in the human, that a toxic dose of Glu or Asp first causes the animal to vomit before continued excitatory stimulation destroys the area postrema-CVO neurons (Olney et al., 1972; Olney and Rhee., 1978).

Based on a study of the literature, several possibilities and hypotheses suggested themselves to the inventor. It appeared likely that Glu and Asp induce emesis in monkeys and dogs (and in humans) by stimulating EAA receptors on the surfaces of area postrema-CVO neurons (the same receptors through which they kill these neurons), which implies that these neurons are connected to an emesis reflex circuit. This raised the question of whether the receptors being stimulated by subcutaneously administered Glu in these animal experiments functioned physiologically by receiving emetic messages from Glu-containing neurons in an emesis reflex circuit. If this were the case, then these Glu-receptive neurons might be an integral link in an emesis reflex circuit, and blocking such receptors with EAA antagonists might interrupt the emesis reflex circuit, and might prevent various other stimuli feeding into the emesis circuit from inducing emesis. Depending on how many types of emetic circuits include an obligatory link comprised of area postrema Glu-receptive neurons, and depending on the types of Glu receptors involved, numerous types of emesis initiated by different stimuli might be suppressed by treatment with a given EAA antagonist. However, if the EAA receptors on the surfaces of area postrema CVO neurons are there only for the purpose of interacting with Glu circulating in the blood, then an EAA antagonist circulating in the blood might block the action of circulating Glu on these neurons without having any effect on circuits regulating other types of emesis.

The experiments described below were undertaken to explore the hypothesis that area postrema CVO neurons are part of a reflex arc from the gut to the brain stem and back to the gut. Based on the results of those experiments, it was discovered that intravenous administration of Glu antagonists can prevent at least some types of emesis by interrupting this reflex arc.

The invention described herein entails control of nausea and vomiting by a mechanism that has never previously been exploited for this purpose. Despite considerable research in the EAA field, and despite many efforts to develop anti-emetic drugs, there are no published reports pertaining to the use of any EAA antagonists as anti-emetic drugs, nor any published reports indicating that EAA antagonists are able to prevent emesis of any kind. Therefore, the invention disclosed herein represents the discovery of an entirely new method for preventing nausea and vomiting, different from any previously described method.

An important feature of this invention is that the locus of action of the EAA antagonists used as described herein is at the level of the "central switchboard" (the emesis center) in the brain stem, where different types of EAA receptors have been shown to participate in the regulation of emesis. Therefore, it is believed by the inventor that several different kinds of vomiting can be controlled by different combinations of EAA antagonists, and that most or all types of vomiting that are not adequately controlled by currently available approaches can be controlled by use of EAA antagonists, alone or in combination with other currently available drugs.

It should be noted that other anti-emetic drugs tend to be useful for controlling only one type of emesis. For example, anti-histaminics are useful only for motion sickness, and not for emesis associated with cancer chemotherapy. 5-HT M receptor antagonists are not effective for motion sickness (Stott et al., 1989) but are somewhat effective for emesis associated with specific cancer chemotherapy drugs, such as cisplatin, that release 5-HT from enterochromaffin cells in the gut. These agents block the emetic stimulus at or near the beginning point, i.e., at the 5-HT receptor site in the gut that receives the original message and sends it through the initial segment of the reflex arc going up to the brain stem. EAA antagonists also block cisplatin-induced emesis, but they do so at the brain stem level by preventing messages transmitted by incoming nerve fibers from being relayed to neurons that transmit outgoing messages to the abdomen, resulting in vomiting. Therefore, the action of EAA antagonists is not limited to a specific mechanism pertaining to the incoming limb of a single reflex arc, as is the case for 5-HT M antagonists; instead, EAA antagonists act at the central switchboard level, where suppression of emesis induction between incoming and outgoing branches of various different emesis reflex arcs appears to be possible. Accordingly, the use of EAA antagonists has potentially wide application for the control of nausea and vomiting.

An additional special feature of this invention is that it takes advantage of the fact that certain Glu antagonists do not penetrate blood brain barriers and cannot enter most regions of the brain proper or the remainder of the CNS. However, they do penetrate select brain regions containing the specific receptors which must be blocked in order to effectively interrupt emesis reflex circuits. The fact that the Glu antagonists do not enter the brain except in the CVO regions signifies that they are much less likely to cause significant side effects than if they were able to interact with Glu receptors throughout the brain, most of which are directly involved in vital functions that are unrelated to emesis regulation.

SUMMARY OF THE INVENTION

This invention relates to a method and a class of pharmaceutical agents for suppressing vomiting, nausea, and other emetic symptoms. The method involves administering to a susceptible mammal a glutamate (EAA) receptor antagonist at an anti-emetically effective dose which does not cause undesirable side effects. Preferred EAA antagonists include those that do not readily cross blood-brain barriers (BBB). One suitable formulation comprises a broad-spectrum antagonist such as kynurenic acid or 7-chlorokynurenate. Other formulations include EAA antagonists that preferentially block NMDA receptors (such as D-AP5) or non- NMDA receptors (such as CNQX), or mixtures thereof that can block both classes of EAA receptors. In lab tests, the agents of this invention were shown to reduce or entirely block the effects of several emetic agents, including cisplatin. Treated animals did not vomit or exhibit lethargy or malaise and did not display any adverse side effects, while control animals consistently displayed lethargy, malaise, and vomiting.

DESCRIPTION OF THE PREFERRED EMBODIMENTS

This invention relates to a pharmacological agent or mixture administered to a patient suffering from nausea or vomiting, or a patient who will receive an emetic dosage of a chemotherapeutic drug or radiation therapy. This pharmacological agent or mixture comprises one or more EAA antagonists which are administered at an anti-emetically effective dose that does not cause adverse side effects.

Preferably, glutamate antagonists used for the purpose of this invention should have a low ability to cross mammalian blood-brain barriers, compared to other EAA antagonists that are known to permeate easily across BBB's. Several such compounds, which have varying affinities for EAA receptors, are listed in Table 1; by contrast, several EAA antagonists that permeate easily through BBB's are listed in Table 2.

The preferred trait of low BBB permeability reduces the extent to which certain anti-emetic EAA antagonists will contact EAA receptors on the surfaces of CNS cells (other than in the vicinity of CVO regions). That will, in turn, minimize any possible adverse side effects. As used herein, "adverse side effects" refers to adverse cellular, physiological, or behavioral effects that are detectable in lab animals (such as vacuole formation or mitochondrial dissolution in certain types of cerebrocortical neurons, as described in Olney et al 1989). It also refers to adverse side effects reported or suffered by humans, such as the psychotic effects that can be caused by phencyclidine, MK-801, ketamine, or tilletamine, which permeate easily through BBB's and therefore are not preferred for use as described herein.

If a specific EAA antagonist leaks through the BBB in limited but significant quantities, it might still be useful as described herein, if it can be administered at a controlled low dosage which exerts an anti-emetic effect without causing adverse side effects in the remainder of the CNS. For example, if an EAA antagonist penetrates the area postrema region of the brain stem, a small amount might diffuse via the extracellular fluid into adjacent areas that are involved in or related to the emesis center, including areas that might be technically considered to be within the BBB-protected portion of the brain or brain stem. Such limited leakage may enhance the anti-emetic effectiveness of the EAA antagonists disclosed herein, without causing unacceptable adverse side effects.

TABLE 1

| | EAA antagonists that do not freely penetrate blood brain barriers | | | | |
|---|---|---|---|---|---|
| | EAA antagonist potency | | | | |
| Antagonist | vs NMDA | vs KA | vs Quis | BBB penetrability | Year first described |
| CGS 19755 | 200* | 0 | 0 | low | 1987 |
| CPP | 200* | 0 | 0 | low | 1987 |
| CPP-ene | 200* | 0 | 0 | moderate | 1989 |
| CGP 37849 | 200* | 0 | 0 | moderate | 1988 |
| ifenprodil | 100 | 0 | 0 | moderate | 1988 |
| SL 82,0715 | 50 | 0 | 0 | moderate | 1989 |
| D-AP5 | 40 | 0 | 0 | very low | 1979 |
| D-AP7 | 13 | 0 | 0 | very low | 1981 |
| α-amino adipate | 5 | 0 | 0 | very low | 1978 |
| CNQX | 5 | 30 | 67 | very low | 1987 |
| DNQX | 10 | 20 | 40 | very low | 1987 |
| 7-Cl-kynurenate | 10 | 4 | 3 | very low | 1988 |
| kynyrenic acid | 4 | 1 | 1 | very low | 1983 |

The antagonists listed are representative agents from each of several categories, none of which freely penetrates BBB; many additional agents with EAA antagonist properties have been described in each category. Antagonist potencies were established in a chick retina assay which has been used by Olney (1989) to screen prototypic EAA receptor agonists (NMDA, KA and Quis) for excitotoxic properties and EAA antagonists for potency in protecting the retina against the excitotoxic action of such agonists. The concentration of antagonist required to totally prevent the toxic action of an agonist was used to compare antagonists for potency. For purposes of illustration, the data were normalized by assigning a potency rating of 1 to kynurenic acid vs KA and all other values were adjusted accordingly.
*These compounds have not been screened in the chick retina assay; their potencies are estimated based on other reported data pertaining to their electrophysiological antagonist properties.

TABLE 2

| EAA antagonists that freely penetrate blood brain barriers | | | | |
|---|---|---|---|---|
| | EAA antagonist potency | | | Year first |
| Antagonist | vs NMDA | vs KA | vs Quis | described |
| MK-801 | 5000 | 0 | 0 | 1986 |
| PCP | 2000 | 0 | 0 | 1982 |
| tilletamine | 200 | 0 | 0 | 1987 |
| procyclidine | 67 | 0 | 0 | 1987 |
| dextrorphan | 40 | 0 | 0 | 1987 |
| ethopropazine | 40 | 0 | 0 | 1987 |
| dextromethorphan | 20 | 0 | 0 | 1986 |
| thiamylal | 13 | 3 | 2 | 1988 |
| thiopental | 7 | 2 | 2 | 1988 |

The antagonists listed are representative agents from each of several categories, all of which freely penetrate BBB; many additional agents with EAA antagonist properties have been described in each category. Antagonist potencies were established in a chick retina assay which has been used by Olney (1989) to screen prototypic EAA receptor agonists (NMDA, KA and Quis) for excitotoxic properties and EAA antagonists for potency in protecting the retina against the excitotoxic action of such agonists. The concentration of antagonist required to totally prevent the toxic action of an agonist was used to compare antagonists for potency. For purposes of illustration, the data were normalized by assigning a potency rating of 1 to kynurenic acid vs KA (see table 1) and all other values were adjusted accordingly.

As used herein, "unacceptable" adverse side effects include side effects that either (1) cause permanent damage to one or more types of neuron in the central nervous system, or (2) are more painful or unpleasant than an emetic response which is being suppressed. In the animal tests done to date, the animals displayed no adverse side effects whatsoever, and it is believed that the agents of the subject invention may be able to suppress many types of emesis with little or no significant adverse side effects. However, as with any pharmacological agent (especially neuropharmacological agents), some adverse side effects may arise, especially at high dosages, and it is up to the treating physician in any specific case to determine whether the potential disadvantages and side effects are worth the benefits, based upon safety and efficacy data gathered during human clinical trials. In particular, the CVO regions of the CNS are involved in certain neuroendocrine regulatory functions which might be perturbed by the EAA antagonists described herein. However, any such effects are likely to be transient and will not cause any lasting problems.

The inventor of the subject invention played a key role in discovering that NMDA antagonists cause pathological changes in certain types of neurons (Olney et al, 1989). In subsequent research, the inventor discovered that certain types of anti-cholinergic agents can prevent or reduce those pathological changes. Those agents and a method for their use are described in a co-pending U.S. patent application entitled "Compounds and Methods for Preventing Neurotoxic Side Effects of NMDA Antagonists," Ser. No. 424,548, the contents of which are incorporated herein by reference. The anti-cholinergic agents tested to date and shown to be effective in reducing the neurotoxicity of NMDA antagonists that penetrate the BBB include scopolamine, atropine, benztropine, benactyzine, biperiden, procyclidine, trihexyphenidyl, and diphenhydramine. Those agents can be co-administered with an NMDA antagonist which penetrates the BBB, such as PCP or MK-801, and will serve as a protective agent to reduce or eliminate the pathological effects that would otherwise be caused by the NMDA antagonist. This will allow the use of NMDA antagonists to prevent brain damage in situations such as severe stroke, perinatal asphyxia, or other types of ischemia, with a higher degree of safety than was previously available.

In a similar manner, the anti-cholinergic agents described in the cited U.S. patent application (Ser. No. 424,548) can be used as protective agents in the subject invention, by co-administering them with the EAA antagonists disclosed herein. This will provide a higher degree of safety against any possible adverse effects from the EAA antagonists. This might allow, for example, the effective but safe use of EAA antagonists that have "moderate" levels of BBB permeability, as indicated in Table 1. It is also likely that anti-cholinergic agents such as scopolamine (which is already used as an anti-emetic agent against certain types of emesis, primarily involving motion sickness) might exert a synergistic effect with the EAA antagonists of this invention. Based on recent discoveries, such as the invention described in U.S. patent application Ser. No. 424,548, it has become clear that there are more interactions between the two main excitatory systems (the EAA system and the cholinergic system) than had previously been recognized. Based on those discoveries, and on scopolamine's effectiveness against motion sickness, administering an EAA antagonist and an anti-cholinergic agent in combination may provide a very powerful anti-emesis treatment.

In one embodiment of this invention, a single broad-spectrum EAA antagonist is used, such as kynurenic acid (Kyn) or an analog thereof, such as 7-chlorokynurenate, which binds to EAA receptors. As used herein, "analog" is used in its conventional pharmaceutical sense; it includes molecules which are structurally similar to a certain molecule, differing by factors such as halide or alkyl group substitutions, altered placement of a certain moiety, etc. For example, DNQX would be regarded as an analog of CNQX, and D-AP7 would be regarded as an analog of D-AP5. Any such analogs, in order to be useful for the purposes of this invention, must be pharmaceutically acceptable, i.e., they must be non-toxic at effective doses, they must be deliverable to the intended site in a suitable pharmaceutical carrier, etc.

The term "broad spectrum" refers to an EAA antagonist (or a mixture of two or more antagonists) which has substantial potency against NMDA receptors and at least one type of non-NMDA receptor (either KA or QUIS). In this context, the phrase "potency against" refers to the ability of an antagonist to prevent or reduce the effects of EAA receptor activation by glutamate, aspartate, or any other naturally occurring EAA transmitter molecules.

In an alternate preferred embodiment of this invention, an EAA antagonist is used which preferentially binds to NMDA receptors, such as D-AP5; alternately, an EAA antagonist is used which preferentially binds to non-NMDA receptors, such as CNQX. In either case, only one class of receptor would be blocked, while the other class would remain undisturbed. As described in Example 1, a selective EAA antagonist which blocks only NMDA receptors has been shown to suppress one type of chemically induced emesis in lab animals, and as described in Example 2, an EAA antagonist has been shown to suppress a different type of chemically induced emesis which directly involves only the KA class of non-NMDA receptors. Therefore, it has been shown that at least some types of emesis can be caused by activating only one type of EAA receptor. It has also been shown that such emesis can be blocked effectively by blocking that particular class of receptor.

As discussed in the Background section, the different types of emesis suffered by humans are not fully understood, and it is not known whether, or to what extent, certain types of emesis may involve activation of NMDA receptors but not non-NMDA receptors (or vice-versa). In general, it is probably preferable to treat any case of emesis with the minimal amount of intervention necessary to provide effective relief, especially since the CVO regions that will be affected are involved in various neuroendocrine regulatory functions. For example, if a specific type of emesis involves activation of NMDA receptors but not non-NMDA receptors, it probably would be preferable to block the NMDA receptors, without blocking the non-NMDA receptors which are involved in normal neuronal processes. Similarly, if non-NMDA receptors alone are involved in a specific type of emesis, it probably would be preferable to block those receptors without blocking the NMDA receptors.

Therefore, the subject invention offers two major benefits. First, it provides a highly useful method for determining whether emesis induced by any type of causative agent involves (1) NMDA receptors only; (2) non-NMDA receptors only; or, (3) both types of receptors. Second, when any specific type of emesis is discovered to involve only one class of receptor (i.e., if it can be suppressed by a selective antagonist such as D-AP5 alone, or by CNQX alone), the subject invention provides a method for treating such cases by blocking only that class of receptor without disturbing or altering the normal functioning of the other class of receptors. This will minimize potential side effects, compared to using broad-spectrum EAA antagonists or mixtures that block both classes of receptors even when one class does not need to be blocked.

In an alternate preferred embodiment of this invention which involves broad-spectrum blockage, which may be necessary in severe cases such as those involving chemotherapy, a mixture of two or more EAA antagonists is used wherein a first antagonist preferentially binds to NMDA receptors, and a second antagonist preferentially binds to non-NMDA receptors. One such mixture, which has been shown to be a highly effective anti-emetic in animal tests, comprises two active ingredients: (1) D-AP5, which blocks NMDA receptors; and (2) CNQX, which preferentially blocks non-NMDA receptors. CNQX is believed to have substantial affinity for both KA and QUIS receptors (see Table 1), as well as a lesser affinity for NMDA receptors. These two agents, or other NMDA and non-NMDA antagonists such as those listed in Table 1, can be mixed together in a single formulation. Alternately, they can be administered separately if desired, preferably within a reasonably brief span of time so that both will exert their effects simultaneously.

The pharmacological agents of this invention can be administered via subcutaneous or intramuscular injection using a single bolus injection, for patients who do not need large quantities, or via intravenous infusion if larger quantities are needed, such as for patients receiving chemotherapy. If injected or infused, they should be mixed with a suitable carrier liquid such as sterile buffered saline.

Some EAA antagonists can be swallowed in capsule, liquid, or emulsion form without suffering an unacceptable reduction in activity; the preferred dosage for oral administration is usually increased compared to injection. If necessary to protect an orally administered EAA antagonist against degradation in the stomach, the antagonist can be placed in a capsule with a coating that does not dissolve until the capsule reaches the small intestines.

The utility and effectiveness of several EAA antagonists as anti-emetic agents have been demonstrated in animal tests described in the Examples. In a series of tests described in Example 1, NMDA (an EAA agonist which activates the NMDA class of EAA receptors) was administered to dogs. It induced vomiting. That emetic response was blocked by subcutaneous (SC) injection of D-AP5, a competitive antagonist which does not penetrate the BBB and which has high affinity for NMDA receptors but not for KA or QUIS receptors. Since neither NMDA nor D-AP5 can cross the BBB, these two results indicate the following:

(1) NMDA receptors on cells outside the BBB are involved in at least some types of emetic response and can causes emesis even if non-NMDA receptors are not activated; and, (2) a competitive antagonist which blocks NMDA receptors only on cells that are not protected by the blood-brain barrier, such as cells in the CVO regions of the CNS, can block an NMDA receptor mediated emetic response.

In Example 2, kainic acid (KA), an agonist which triggers the KA class of non-NMDA receptors, was used to induce vomiting in dogs. That response was blocked by kynurenic acid (Kyn), an EAA antagonist which does not penetrate the BBB, but which acts at both NMDA and non-NMDA receptors.

In Example 3, glutamate was administered to dogs. It activated both NMDA and non-NMDA receptors in the CVO regions (but not inside the remainder of the CNS, since glutamate does not penetrate the BBB). An emetic response occurred, which could not be blocked by D-AP5 even at relatively high doses. However, the emetic response could be blocked by Kyn. These results, together with the results of Example 2, suggest that both NMDA and non-NMDA receptors may play a role in some types of EAA-mediated emesis. In order to prevent that type of emesis, both types of receptors must be blocked by a broad-spectrum EAA antagonist, or by a mixture of antagonists which, acting together, have broad-spectrum activity.

The preliminary results involving dogs led to a more extensive series of tests involving ferrets. As described in Example 4, experiments were performed on ferrets using cisplatin, a chemotherapeutic drug which has a powerful emetic effect. Four ferrets (a control group) received cisplatin. All four displayed persistent malaise and obviously did not feel well; none were playful, and none sought or ate any food. One control animal did not vomit, but the other three vomited repeatedly during the observation period. Nine test animals were treated with cisplatin, and with Kyn at varying doses either by bolus (one-shot) injection or by continuous IV infusion. All of the ferrets treated by continuous infusion displayed playful behavior, sought and ate food, did not appear ill, and did not vomit. Three of the ferrets treated by bolus injection vomited once or twice and showed transient malaise; however, only one appeared to be as ill as the control animals.

In late 1987, Honore et al reported that a newly discovered compound, CNQX, could block non-NMDA receptors with high affinity. CNQX does not cross the BBB. The inventor obtained a sample of CNQX (Ferrosan Pharmaceuticals, Denmark) and determined, in an in vitro assay using retinas from chick embryos (Olney et al, 1986), that it is approximately 30 times more powerful than Kyn in blocking non-NMDA receptors.

Since suitable agents such as D-AP5 are already available that can block NMDA receptors without crossing the BBB, a mixture of CNQX and D-AP5 was tested to see whether the mixture had anti-emetic properties. In these tests, described in Example 5, the dosage of cisplatin was increased to 10 mg/kg IV, since only 3 out of 4 of the control animals vomited when 8 mg/kg was used in Example 4. This increased the stringency of the test. Five control animals (ferrets) were treated. All five displayed repeated vomiting, with 5 to 10 vomiting episodes each within the first 2 hours. All appeared ill throughout the 5 hour observation period.

Five test animals were treated by intravenous infusion of a mixture of CNQX and D-AP5. All 5 were completely free of vomiting throughout the 5 hour observation period. Some were playful and sought and ingested food and water; some appeared somnolent during part of the observation period, but none displayed any clear discomfort. There was no indication of any significant side effects. This result confirms that vomiting and nausea induced by a powerful emetic agent can be prevented by drugs that exert blocking activity against both NMDA and non-NMDA receptors, even though the drugs used do not cross the blood-brain barriers.

As mentioned above, it appears that the emesis center in the brain stem mediates various emetic reflex arcs that initially involve non-EAA receptors, such as dopamine, serotonin, histamine, or cholinergic receptors. Based on the experimental results described herein, coupled with previous information, it appears that EAA receptors in the emesis center are involved as integral components of various different types of arcs. Since there may be many segments in a reflex circuit, analogous to successive links in a chain, both EAA receptors and non-EAA receptor systems may be integral components of any given circuit. The important requirement for achieving an anti-emetic effect with EAA antagonists of this invention is that there be an EAA receptor link in the circuit which lies outside the BBB, so that it can be contacted by EAA antagonists circulating in the blood. Regardless how many other transmitter receptors participate in any given reflex arc, if an EAA antagonist blocks transmission through an EAA link in the circuit, it will prevent the initial stimulus from leading to an emetic response.

In addition, EAA antagonists, when used as described herein, will allow researchers to study and evaluate the roles that glutamate, aspartate, and EAA receptors play in emesis that is initially triggered by various emetic factors.

It should also be recognized that extensive research is actively being done on EAA antagonists, and reports have appeared during each of the past few years identifying EAA antagonists with varying combinations of receptor affinities and BBB permeabilities. Several such compounds which have appeared recently are listed in Tables 1 and 2. Other EAA antagonists will surely be discovered in the future, including various compounds that do not penetrate the BBB in high quantities. Such antagonists can be screened for anti-emetic activity using no more than routine experimentation. Compounds which perform effectively as anti-emetics can be further analyzed to determine whether they cause adverse effects in animals, and if so, at what dosages, using the methods described herein and in Olney et al 1989. EAA antagonists which have a wide margin of safety between the anti-emetic effective dosage, and the dosage that causes significant adverse side effects, can be used as described herein for the purposes of this invention, subject to human clinical testing to ensure that any side effects are acceptably small. Such antagonists may have higher affinities for one or more classes of EAA receptors, and as such, they may comprise patentable improvements over the antagonists known today. However, such improvements will fall within the teachings of this invention and the coverage of the claims, if they are used as anti-emetic agents in the manner and for the purposes described herein.

EXAMPLES

Example 1: Emesis Induction by NMDA; Blockage by D-AP5

NMDA, an EAA agonist which does not penetrate the BBB and which activates NMDA receptors but not non-NMDA receptors, was administered intravenously (IV) to dogs at doses in the vicinity of 5 mg/kg. The vomit reflex in dogs is sensitive and rapidly transient, and vomiting can be induced by NMDA at dosages that cause no lasting symptoms. Therefore, each dog (all were young adults) was used for more than one experiment. Typically, one or more tests would be done using NMDA to determine an effective dosage for an individual dog. After the dose was established, an experiment was conducted on a subsequent day in which the dog also received 2 mg/kg D-AP5 subcutaneously (SC), along with the NMDA. On the day after that, NMDA was administered alone, to ensure that the emetic response was unchanged and the dog had not developed tolerance or sustained damage to the emesis-mediating reflexes.

The D-AP5 blocked the emesis response in all dogs. Since D-AP5 cannot cross the BBB, these results indicate the following:

(1) NMDA receptors on cells outside the BBB are involved in at least some types of emetic response and can causes emesis even if non-NMDA receptors are not activated; and, (2) a competitive antagonist which blocks NMDA receptors only on cells outside the BBB, such as cells in the CVO regions of the CNS, can block an NMDA receptor-mediated emetic response.

Example 2 Emesis Induction by KA; Blockage by Kyn

Kainic acid (KA), an EAA agonist which triggers the KA class of non-NMDA receptors, was administered to dogs at dosages in the vicinity of 0.5 mg/kg SC. On certain days, the dogs also received kynurenic acid (Kyn), an EAA antagonist that does not readily penetrate the BBB. All of the animals suffered an emetic response when KA was administered without Kyn; however, emesis was blocked by 50 mg/kg Kyn SC.

These results indicate that:

1. some types of emesis are mediated by non-NMDA EAA receptors on cells outside the BBB, even if NMDA receptors are not directly triggered; and, 2. an antagonist that blocks KA receptors only on cells outside the BBB can block a KA receptor-mediated emetic response.

Example 3: Emesis Induction by Glutamate

Glutamate was administered to dogs (150 mg/kg IV). It activated both NMDA and non-NMDA receptors in the CVO regions, but not inside the remainder of the CNS, since glutamate does not penetrate the BBB. An emetic response was observed in all animals. This response could not be blocked by D-AP5, even at doses up to 25 mg/kg SC. However, it could be blocked by Kyn, a broad-spectrum EAA antagonist that blocks both NMDA and non-NMDA receptors, at a dosage of 75 mg/kg SC. These results indicate that both NMDA and non-NMDA receptors can play a role in some types of emesis, and both categories of receptors must be blocked in order to prevent those types of emesis.

Example 4: Emesis Induction by Cisplatin; Blockage by Kyn

Four ferrets (a control group) received 8 mg/kg IV cisplatin, a chemotherapeutic drug which has a powerful emetic effect. All four control animals displayed persistent malaise and obviously did not feel well; none was playful, and none sought or ate any food. One control animal did not vomit, but the other three vomited repeatedly during the observation period (five hours; most vomiting occurred during the first two hours).

Nine ferrets were treated with cisplatin (8 mg/kg IV), and with Kyn, either by bolus (one-shot) injection using 150 mg/kg, or by continuous IV infusion using 50 mg/kg/hour. All of the ferrets treated by continuous infusion displayed playful behavior, sought and ate food, did not appear ill, and did not vomit. Three of the ferrets treated by bolus injection vomited once or twice and showed transient malaise; however, only one appeared to be as ill as the control animals.

Example 5: Emesis Induction by Cisolatin; Blockage by D-AP5/CNQX

Honore et al 1987 and 1988 reported that CNQX, which does not cross the BBB, could block non-NMDA receptors with high affinity. The inventor obtained a sample from Ferrosan Pharmaceuticals of Denmark and determined, in an assay using chick retinas (Olney et al 1986) that it is approximately 30 times more powerful than Kyn in blocking non-NMDA receptors.

Since suitable agents such as D-AP5 are available that can block NMDA receptors without crossing the BBB, a mixture of CNQX and D-AP5 was tested to see whether a mixture of an NMDA antagonist and a non-NMDA antagonist would have anti-emetic properties. The dosage of cisplatin was increased to 10 mg/kg IV, since only 3 out of 4 of the control animals vomited when 8 mg/kg was used as described in Example 4. This increased the stringency of the test.

Five control animals (ferrets) were treated. All five displayed 5 to 10 vomiting episodes each within the first 2 hours, and all appeared ill throughout the observation period, which lasted five hours.

Five test animals were treated by cisplatin, 10 mg/kg IV, followed by intravenous infusion of a mixture of 15 mg/kg/hr CNQX and 5 mg/kg/hr D-AP5. All 5 were completely free of vomiting throughout the 5 hour observation. Some were playful and sought and ingested food and water; some appeared somnolent during part of the observation period, but none displayed any clear discomfort. There was no indication of any significant side effects. This result confirms that vomiting and nausea induced by a powerful emetic agent can be prevented by EAA antagonists that do not cross the blood-brain barriers.

Thus, it has been demonstrated that various types and mixtures of EAA antagonists can reduce or eliminate at least some types of emesis. Judging from lab animal behavior, these pharmacological agents also reduced or eliminated nausea, and did not cause any adverse side effects. This invention therefore satisfies all of the objectives set forth above.

As will be recognized by those skilled in the art, various modifications can be made to the specific embodiments described here. Such changes, if they do not depart from the scope and teachings of the subject invention, are deemed to be covered by this invention, which is limited only by the claims below.

REFERENCE

Bermudez, J. et al, "The anti-emetic potential of the 5-hydroxytryptamine3 receptor antagonist BRL 43694," *Br. J. Cancer* 58: 644-650 (1988).

Boast, C. A., "Neuroprotection after brain ischemia: role of competitive NMDA antagonists," *Neurology and Neurobiology* 46: 691-698 (1988).

Borison, H. L. and Wang, S.C., "Physiology and pharmacology of vomiting," *Pharmacological Reviews* 5: 193-230 (1953).

Borison, H. L. and Brizzee, K. R., "Morphology of emetic chemoreceptor trigger zone in cat medulla oblongata," *Proc. Soc. Exo. Biol. Med.* 77: 38-42 (1951)

Cassidy, J. et al, "Pharmacokinetics and anti-emetic efficacy of BRL 43694, a new selective 5HT-3 antagonist," *Br. J. Cancer* 58: 651-653 (1988).

Drejer, J. and Honore, T., "New quinoxalinediones show potent antagonism of quisqualate responses in cultured mouse cortical neurons," *Neurosci. Letters* 87: 104-108 (1988).

Florczyck, A. P., et al, "Cisplatin induced emesis in the
ferret: a new animal model," *Cancer Treatment Reports* 66: 187-190 (1982).

Goodman, L. S. and Gilman, A., The Pharmacological Basis of Therapeutics. 5th ed., (Macmillan, N.Y., 1975)

Hawthorn, J. et al, "The role of the abdominal visceral innervation and 5-HT M receptors in vomiting induced by the cytotoxic drugs cyclophosphamide and cisplatin in the ferret," *Ouarterly J. Exp. Physiology* 73: 7-21 (1988).

Herrling, P. L., et al, "NMDA antagonistic properties of the enantiomers of CPP and CPP-ene," *Soc. Neurosci. Abstr.* 15: 327 (1989).

Honore, T., et al., "Potent and competitive antagonism at non-NMDA receptors by FG 9041 and FG 9065," *Soc. Neurosci. Abstr.* 3: 383 (1987).

Honore, T. et al, "Quinoxalinediones: potent competitive non-NMDA glutamate receptor antagonists," *Science* 241: 701-703 (1988)

Levey, S., et al, "Serum glutamic acid levels and the occurrence of nausea and vomiting after intravenous administration of amino acid mixtures," *J. Lab. Clin. Med.* 34: 1238-1249 (1949).

Madden, S. C. et al, "Tolerance to amino acid mixtures and casein digests given intravenously; Glutamic acid responsible for reactions," *J. Exo. Med.* 81: 439-448 (1945).

Miner, E. D. and Sanger, G. L. "Inhibition of cisplatin-induced vomiting by selective 5-hydroxytryptamine M-receptor antagonism," *J. Pharmacol.* 88: 497-502 (1986).

Olney, J. W. et al, "Glutamate-induced brain damage in infant primates," *J. Neurocathol. Exo. Neurol.* 31: 464-488 (1972).

Olney, J. W. and Rhee, V., "Neurotoxic effects of glutamate on primate area postrema," *J. Neuropath. Exp. Neurol.* 37: 669 (1978).

Olney, J. W., et al, "The anti-excitotoxic effects of certain anestehtics, analgesics, and sedative-hypnotics," *Neuroscience Letters* 68: 29-34 (1986).

Olney, J. W., "Excitatory amino acids and neuropsychiatric disorders," *Biol. Psychiatry* 26: 505-525 (1989).

Olney, J. W., et al, "Pathological changes induced in cerebrocortical neurons by phencyclidine and related drugs," *Science* 244: 1360-1362 (1989).

Rapoport, S. I., *Blood-brain barrier in physiology and medicine* (Raven Press, N.Y., 1976)

Stott, J. R. R. et al, "The effect on motion sickness and oculomotor function of GR 38032F, a 5-HT3 receptor antagonist with anti-emetic properties," *Br. J. Clin. Pharmacol.* 27: 147-157 (1989).

Unna, K. and Howe, E. E., "Toxic effects of glutamic and aspartic acid," *Fed. Proc.* 4: 138 (1945).

I claim:

1. A method fr suppressing emesis mediated by activation of excitatory amino acid receptors on the surfaces of meurons in brain regions accessible to blood-borne molecules that do not freely penetrate blood-brain barriers comprising administering to a susceptible mammal, an anti-emetically effective dosage of an excitatory amino acid antagonist which is capable of inhibiting excitatory activity at such receptors.

2. The method of claim 1, wherein the excitatory amino acid antagonist has a low ability to cross mammalian blood-brain barriers.

3. The method of claim 1, wherein the excitatory amino acid antagonist blocks NMDA receptors and non-NMDA receptors on the surfaces of neurons in the central nervous system.

4. The method of claim 2, wherein the excitatory amino acid antagonist blocks NMDA receptors and non-NMDA receptors on the surfaces of neurons in the central nervous system.

5. The method of claim 4, wherein the EAA antagonist comprises kynurenic acid or an analog thereof which functions as an EAA antagonist.

6. The method of claim 1, wherein the excitatory amino acid antagonist comprises a quinoxalinedione which functions as an excitatory amino acid antagonist that blocks non-NMDA receptors on the surfaces of neurons in the central nervous system.

7. The method of claim 1, wherein the EAA antagonist comprises D-AP5 or an analog thereof which functions as an EAA antagonist that blocks NMDA receptors.

8. The method of claim 6, wherein the quinoxalinedione is selected from the group consisting of 6nitro-7-cyano-guinoxaline-2,3-dione (common name CNQX), 6,7-dinitro-quinoxaline-2,3,-dione (common name DNQX), and analogs thereof which function as excitatory amino acid antagonists.

9. The method of claim 1, wherein the EAA antagonist is selected from the group consisting of CGP 37849, CPP-ene ifenprodil, SL 82,0715, and analogs thereof.

10. The method of claim 1, wherein the EAA antagonist is administered in conjunction with an anti-cholinergic drug which functions as a protective agent to reduce or eliminate any neurotoxic effects that would be caused by the EAA antagonist in the absence of the anti-cholinergic drug.

11. The method of claim 10, wherein the anti-cholinergic drug is selected from the group consisting of scopolamine, atropine, benztropine, benactyzine, biperiden, procyclidine, trihexphenidyl, and diphenhydramine.

12. A method for suppressing emesis, comprising administering to a susceptible mammal an anti-emetically effective dosage of a first EAA antagonist which blocks NMDA receptors and a second EAA antagonist which blocks at least one type of non-NMDA receptor.

13. The method of claim 12, wherein the first EAA antagonist has a sufficiently low ability to cross mammalian blood-brain barriers so that it will not contact EAA receptors in a mammalian central nervous system, except in circumventricular organs or in regions adjacent to circumventricular organs, in quantities sufficient to cause unacceptable adverse side effects.

14. The method of claim 12, wherein the second EAA antagonist has a sufficiently low ability to cross maintain blood-brain barriers so that it will not contact EAA receptors in a mammalian central nervous system, except in circumventricular organs or in regions adjacent to circumventricular organs, in quantities sufficient to cause unacceptable adverse side effects.

15. The method of claim 12, wherein the first EAA antagonist comprises D-AP5 or an analog thereof which functions as an EAA antagonist that blocks NMDA receptors.

16. The method of claim 12, wherein the second EAA antagonist comprises a quinoxalinedione which functions as an EAA antagonist that blocks non-NMDA receptors.

17. The method of claim 12, wherein the first and second EAA antagonists are administered in conjunction with an anti-cholinergic drug which functions as a protective agent to reduce or eliminate any neurotoxic effects that would be caused by an EAA antagonist in the absence of the anti-cholinergic drug.

18. The method of claim 12, wherein the anti-cholinergic drug is selected from the group consisting of scopolamine, atropine, benztropine, benactyzine, biperiden, procyclidine, trihexyphenidyl, and diphenhydramine.

* * * * *

UNITED STATES PATENT AND TRADEMARK OFFICE
CERTIFICATE OF CORRECTION

PATENT NO. : 5,039,528
DATED : August 13, 1991
INVENTOR(S) : John W. Olney

It is certified that error appears in the above—identified patent and that said Letters Patent is hereby corrected as shown below:

Column 10, line 15, delete "kynyrenic" and insert --kynurenic--.

Column 16, line 8, after "2" insert --:--

Column 16, line 8, delete "Blockaqe" and insert --Blockage --.

Column 18, line 50, delete "fr suppresing" and insert --for suppressing--.

Column 18, line 52, delete "meurons" and insert --neurons--.

Column 19, line 15, delete "cyano-guinoxaline" and insert -- cyano-quinoxaline--.

Column 19, line 15, delete "(common name CNQX)".

Column 19, lines 16 and 17, delete "(common name DNQX)".

UNITED STATES PATENT AND TRADEMARK OFFICE
CERTIFICATE OF CORRECTION

PATENT NO. : 5,039,528

DATED : August 13, 1991

INVENTOR(S) : John W. Olney

It is certified that error appears in the above-identified patent and that said Letters Patent is hereby corrected as shown below:

Column 8, line 14, "6nitro" should read --6-nitro--.

Signed and Sealed this

Twenty-second Day of December, 1992

*Attest:*

DOUGLAS B. COMER

*Attesting Officer*    *Acting Commissioner of Patents and Trademarks*